(12) United States Patent
Speier et al.

(10) Patent No.: US 6,570,381 B1
(45) Date of Patent: May 27, 2003

(54) NUCLEAR MAGNETIC RESONANCE WELL LOGGING METHOD AND APPARATUS

(75) Inventors: Peter Speier, Stafford, TX (US); Krishnamurthy Ganesan, Sugar Land, TX (US); Boqin Sun, Sugar Land, TX (US); Reza Taherian, Stafford, TX (US); Christian Straley, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/276,049

(22) Filed: Mar. 25, 1999

(51) Int. Cl.[7] ................................................. G01V 3/00
(52) U.S. Cl. ........................................................ 324/303
(58) Field of Search ......................................... 324/303

(56) References Cited

U.S. PATENT DOCUMENTS

| | | | |
|---|---|---|---|
| 4,438,400 A | | 3/1984 | Patt |
| 5,023,551 A | * | 6/1991 | Kleinberg et al. ............ 324/303 |
| 5,055,788 A | | 10/1991 | Kleinberg et al. |
| 5,153,514 A | | 10/1992 | Griffin et al. |
| 5,796,252 A | * | 8/1998 | Kleinberg et al. ............ 324/303 |
| 6,121,774 A | * | 9/2000 | Sun et al. ..................... 324/303 |
| 6,204,663 B1 | * | 3/2001 | Prammer ...................... 324/303 |

FOREIGN PATENT DOCUMENTS

WO 98/43064 10/1998

OTHER PUBLICATIONS

Combined Search and Examination Report Sections 17 and 18(3), Oct. 25, 2000, United Kingdom Patent Office.

R.L. Kleinberg, A. Sezginer, D.D. Griffin, and M. Fukuhara, "Novel NMR Apparatus for Investigating an External Sample," J. Mag. Res., 97, 466–485, (1992).

I.P. Gerothanassis, "Methods of Avoiding The Effects Of Acoustic Ringing In Pulsed Fourier Transform Nuclear Magnetic Resonance Spectroscopy", Progress in NMR Spectroscopy, vol. 19, pp. 276–329 (1987).

S. Zhang, X. Wu, and M. Mehring, "Elimination Of Ringing Effects In Multiple–Pulse Sequences", Chemical Physics Letters, vol. 173, No. 5.6, pp. 481–484 (1990).

A.A.V. Gibson and R. E. Raab, "Proton NMR and peizo-electricity in tetramethylammonium chloride," J. Chem. Phys. 57, 4688–4693, (1972).

M.L. Buess, and G.L. Peterson, "Acoustic ringing effects in pulsed magnetic resonance probes," Rev. Sci. Instrum., 49, 1151–1155, (1978).

E. Fukushima, and S.B.W. Roeder, "Spurious ringing in pulse NMR," J. Mag. Resonance, 33, 199–203, (1979).

* cited by examiner

Primary Examiner—Edward Lefkowitz
Assistant Examiner—Dixomara Vargas
(74) Attorney, Agent, or Firm—Kevin P. McEnaney; Brigitte L. Jeffery (57) ABSTRACT

The present invention relates generally to a nuclear magnetic resonance apparatus and method for substantially eliminating the effects of phase coherent acoustic ringing in borehole logging. A series of cycles of measurement pulse sequences are applied to the formation surrounding the borehole. Each pulse sequence includes an RF excitation pulse and several RF refocusing pulses. Spin echoes are received that contain spurious ringing signals from the excitation and refocusing pulses. Spin echo signals from corresponding spin echoes of each cycle are combined and substantially cancel the spurious ringing from the excitation and refocusing pulses of the pulse sequences.

54 Claims, 9 Drawing Sheets

NUCLEAR MAGNETIC RESONANCE WELL LOGGING METHOD AND APPARATUS

FIELD OF THE INVENTION

This invention relates to techniques and apparatus for determining characteristics of earth formations surrounding a borehole and, more particularly, to nuclear magnetic resonance borehole logging that utilizes pulse sequences which improve performance.

BACKGROUND OF THE INVENTION

General background of nuclear magnetic resonance (NMR) well logging is set forth, for example, in U.S. Pat. No. 5,023,551. Briefly, in NMR operation the spins of nuclei polarize along an externally applied static magnetic field, assumed to be in the z direction. The vector sum of the magnetic moment from individual nuclei is a macroscopic magnetic dipole called the magnetization, $M_0$. The magnetization is normally aligned with the static magnetic field, but the equilibrium situation can be disturbed by a pulse of an oscillating magnetic field (e.g. an RF pulse generated by an RF antenna), which rotates the magnetization away from the static field direction. The length of the RF pulse can be adjusted to achieve a prescribed rotation angle, such as 90 degrees, 180 degrees, etc. After rotating, two things occur simultaneously. First, the spins precess around the static field at the Larmor frequency, given by $\omega_0 = \gamma B_0$, where $B_0$ is the strength of the static field and $\gamma$ is the gyromagnetic ratio. For hydrogen nuclei, $\gamma/2\pi = 4258$ Hz/Gauss, so, for example, for a static field of 235 Gauss, the frequency of precession would be 1 MHz. Second, the spins return to the equilibrium direction according to a decay time T1, the spin lattice relaxation time. Also associated with the magnetization is a second relaxation called the spin-spin relaxation with a decay time T2.

A widely used technique for acquiring NMR data both in the laboratory and in well logging, uses an RF pulse sequence known as the CPMG (Carr-Purcell-Meiboom-Gill) sequence. As is well known, after a wait time that precedes each pulse sequence, known as polarization time, a ninety degree pulse rotates the magnetization to the x-y plane. The spins begin to precess around $B_0$ and dephase. After a certain time delay, a one hundred eighty degree pulse is applied to cause the spins which are dephasing in the transverse plane to refocus. Refocusing leads to an echo that is detected by the NMR instrument. By repeated application of one hundred eighty degree pulses, a series of "spin echoes" appear, and the train of echoes is measured and processed.

It has been recognized that "ringing" is a problem encountered when using pulsed nuclear magnetic resonance techniques. There are two types of spurious ringing in pulsed NMR. The first type is electronic ringing which arises from the transient effects of a resonance electronic circuit, and is determined by the characteristics of the resonance circuit. The electronic ringing can be substantially reduced using time-controlled hardware such as Q-switching approaches. The second type of spurious ringing arises from exciting the acoustic resonances in or around the RF antenna structure. [See A. A. V. Gibson and R. E. Raab, "Proton NMR and piezoelectricity in tetramethylammonium chloride," J. Chem. Phys. 57, 4688–4693, (1972); M. L. Buess, and G. L. Peterson, "Acoustic ringing effects in pulsed magnetic resonance probes," Rev. Sci. Instrum., 49, 1151–1155, (1978); E. Fukushima, and S. B. W. Roeder, "Spurious ringing in pulse NMR," J. Mag. Resonance, 33, 199–203, (1979); and R. L. Kleinberg, A. Sezginer, D. D. Griffin, and M. Fukuhara, "Novel NMR Apparatus for Investigating an External Sample," J. Mag. Res., 97, 466–485, (1992).] This is magnetoacoustic ringing, and can last up to several milliseconds. It appears whenever the frequency of the applied RF current matches at least one of acoustic resonance modes of the RF antenna or its surrounding structure. Both types of ringing are phase coherent with the applied RF pulse and therefore can not be canceled, unlike incoherent noise, by stacking repeated measurements. [Techniques for dealing with the problems of ringing in laboratory equipment are disclosed in U.S. Pat. No. 4,438,400 and in the following publications: I. P. Gerothanassis, "Methods Of Avoiding The Effects Of Acoustic Ringing In Pulsed Fourier Transform Nuclear Magnetic Resonance Spectroscopy", Progress in NMR Spectroscopy, Vol. 19, pp. 276–329, 1987 (see Section 9.3 and see Note Added In Proof with regard to sequences of interest as used in laboratory spectrometry with single echo sequences); and S. Zhang, X. Wu, and M. Mehring, "Elimination Of Ringing Effects In Multiple-Pulse Sequences", Chemical Physics Letters, Vol. 173, No. 5.6, pp. 481–484, 1990.]

The amplitude of the ringing signal can be large enough to saturate the receiver circuitry, making its response to the CPMG echo signal nonlinear. Magnetoacoustic ringing can be reduced by selecting proper material for the RF antenna and its surrounding structure (see, for example, U.S. Pat. No. 5,153,514), but it is very difficult to completely eliminate acoustic ringing by mechanical methods alone, particularly in well logging equipment that has design constraints relating to its adaptability for the borehole environment. This ringing can be a major obstacle for measuring parameters such as total porosity in magnetic resonance logging.

It is among the objects of the present invention to provide a technique and apparatus for substantially eliminating the effects of phase coherent acoustic ringing in nuclear magnetic resonance well logging.

SUMMARY OF THE INVENTION

In accordance with a form of the method of the invention, there is disclosed a technique for obtaining nuclear magnetic resonance measurements from formations surrounding an earth borehole, comprising the following steps: providing a logging device that is moveable through the borehole and through formations in which a static magnetic field is present; producing, from the logging device, a series of cycles of pulse sequences in the formations, each of the pulse sequences including an RF excitation pulse and several RF refocusing pulses; receiving, at the logging device, spin echoes from the formations to produce spin echo signals that may include spurious ringing signals from the excitation and refocusing pulses; and combining spin echo signals from corresponding spin echoes of each of the cycles of pulse sequences to obtain combined spin echo signals in which spurious ringing from the excitation pulses and refocusing pulses of the pulse sequences is substantially cancelled. The static magnetic field can be earth's magnetic field or a static magnetic field produced at the logging device.

In a preferred embodiment of the invention, the steps of producing cycles of pulse sequences and combining spin echo signals include manipulating the polarities of the excitation and refocusing pulses to obtain the substantial cancellation of the spurious ringing from the excitation and refocusing pulses.

Also in a preferred embodiment of the invention, the series of cycles of pulse sequences comprises four cycles of pulse sequences. In a form of this embodiment, the step of combining spin echo signals from corresponding spin echoes of each of the cycles of pulse sequences to obtain combined spin echo signals comprises combining corresponding spin echo signals from two of cycles and subtracting the spin echo signals from the other two of the cycles. Also in this form of the embodiment, all the spin echo signals of two of the four cycles have a polarity that is opposite to that of all the spin echo signals of the other two of the four cycles.

In a further embodiment of the invention, the step of producing a series of cycles of pulse sequences in the formations further includes producing an RF inverting pulse in some of the cycles of pulse sequences, and the step of receiving spin echoes from the formations to produce spin echo signals includes receiving spin echoes to produce spin echo signals that may includes spurious ringing signals from the inverting pulses, and the combining step includes combining spin echoes of each of the cycles of pulse sequences to obtain combined spin echoes in which spurious ringing from the inverting pulses of the pulse sequences is also substantially cancelled. In a form of this embodiment, the inverting pulses are implemented before the excitation pulses of their respective cycles. The excitation and inverting pulses can be combined into a single pulse in each of a plurality of the pulse sequences.

In one preferred form of the invention, the excitation pulses are 90 degree pulses and the refocusing and inverting pulses are 180 degree pulses.

In an embodiment of the invention, the four sequences are constructed using a set of specific construction rules (detailed hereinbelow) that define the phase relationships of the RF pulses used in the sequences. One example of a four phase cycle that satisfies these rules, is $$x[y]^{n+1}, \underline{x}[y]^{n+1}, xx[y]^n, \underline{xx}[y]^n,$$

where the first letter represents the rf carrier phase of the RF excitation pulse and subsequent letters represent the rf carrier phases of the RF refocusing pulses (x=0 degrees, y=90 degrees, $\underline{x}$=180 degrees, $\underline{y}$=270 degrees). All phases are measured relative to an (arbitrarily chosen) reference phase. Examples of other possible forms of this embodiment include:

$$x[\underline{y}]^{n+1}, \underline{x}[\underline{y}]^{n+1}, xx[y]^n, \underline{xx}[y]^n$$

$$x[\underline{y}]^{n+1}, \underline{x}[\underline{y}]^{n+1}, xx[y]^n, \underline{xx}[y]^n$$

$$x[y]^{n+1}, \underline{x}[y]^{n+1}, xx[y]^n, \underline{xx}[y]^n$$

$$x[y]^{n+1}, \underline{x}[y]^{n+1}, xx[\underline{y}]^n, \underline{xx}[\underline{y}]^n$$

$$x[\underline{y}]^{n+1}, \underline{x}[\underline{y}]^{n+1}, xx[\underline{y}]^n, \underline{xx}[\underline{y}]^n$$

$$x[\underline{y}]^{n+1}, \underline{x}[\underline{y}]^{n+1}, xx[\underline{y}]^n, \underline{xx}[\underline{y}]^n$$

$$x[y]^{n+1}, \underline{x}[y]^{n+1}, xx[\underline{y}]^n, \underline{xx}[\underline{y}]^n$$

$$x[y]^{n+1}, \underline{x}[y]^{n+1}, xx[\underline{y}]^n, xx[\underline{y}]^n$$

$$x[y]^{n+1}, x[\underline{y}]^{n+1}, xx[\underline{y}]^n, xx[y]^n$$

and $$0° \ 45° \ [0°]^n, \ 180° \ 45° \ [0°]^n, \ 0° \ -45° \ [0°]^n, \ 180° \ -45° \ [0°]^n$$

Further features and advantages of the invention will become more readily apparent from the following detailed description when taken in conjunction with the accompanying drawings.

DETAILED DESCRIPTION

Figure 1:
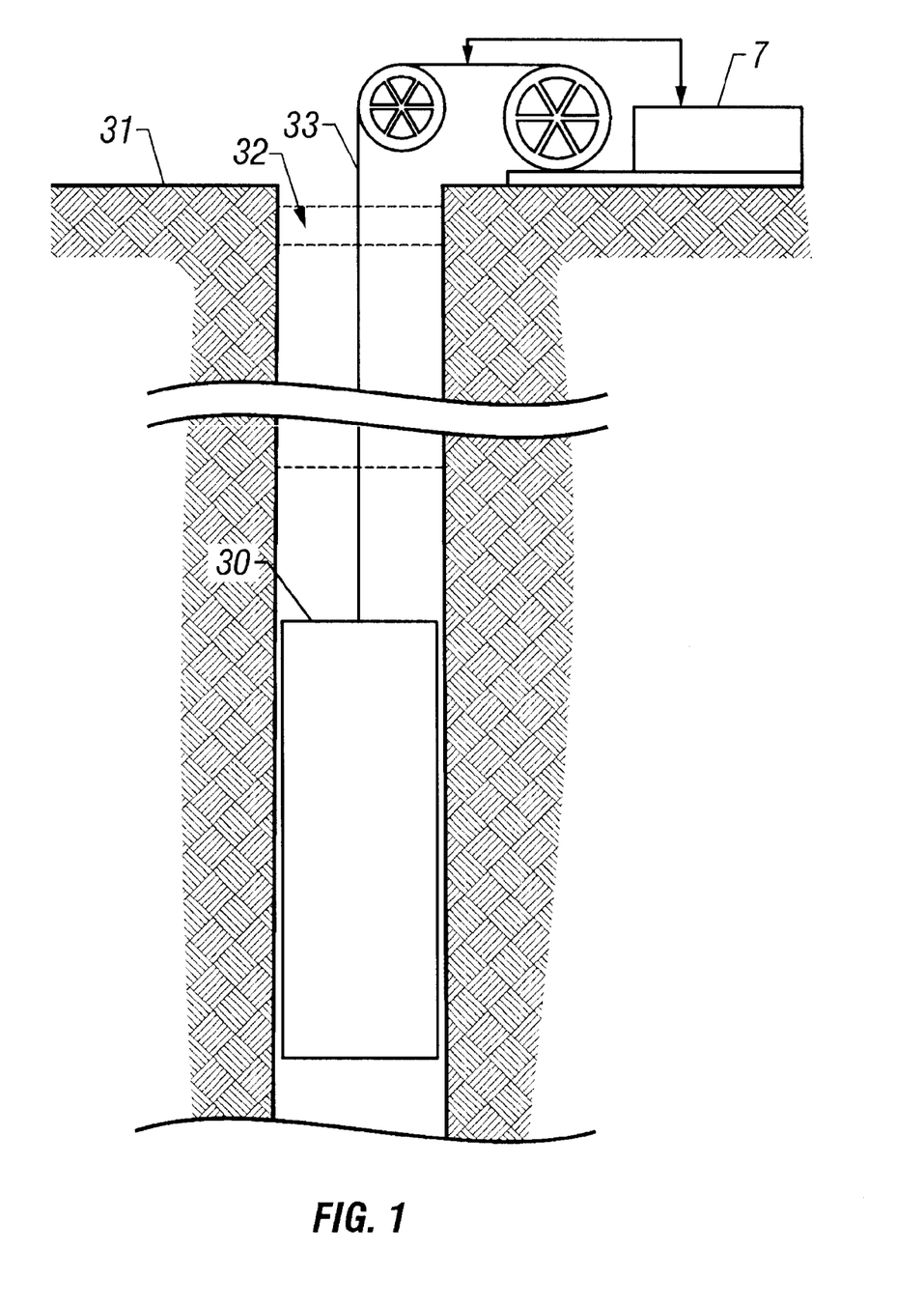
FIG. 1 is a schematic diagram, partially in block form, of a well logging apparatus that can be used in practicing embodiments of the invention.

Referring to FIG. 1, there is shown an apparatus for investigating subsurface formations 31 traversed by a borehole 32, which can be used in practicing embodiments of the invention.

An investigating apparatus or logging device 30 is suspended in the borehole 32 on an armored cable 33, the length of which substantially determines the relative depth of the device 30. The cable length is controlled by suitable means at the surface such as a drum and winch mechanism (not shown). Surface equipment, represented at 7, can be of conventional type, and can include a processor subsystem and communicates with the downhole equipment.

The logging device can be any suitable nuclear magnetic resonance logging device, for example of the type described in U.S. Pat. No. 5,055,788 for use in wireline logging applications, or of a type that can be employed in measurement while drilling applications. As described in the just referenced Patent, the device 30 includes a magnet array for producing a static magnetic field in the formations, and a radio frequency (RF) antenna for producing pulses of RF magnetic field in the formations and for receiving the spin echoes from the formations. Alternatively, the static magnetic field can be earth's magnetic field.

Figure 2:
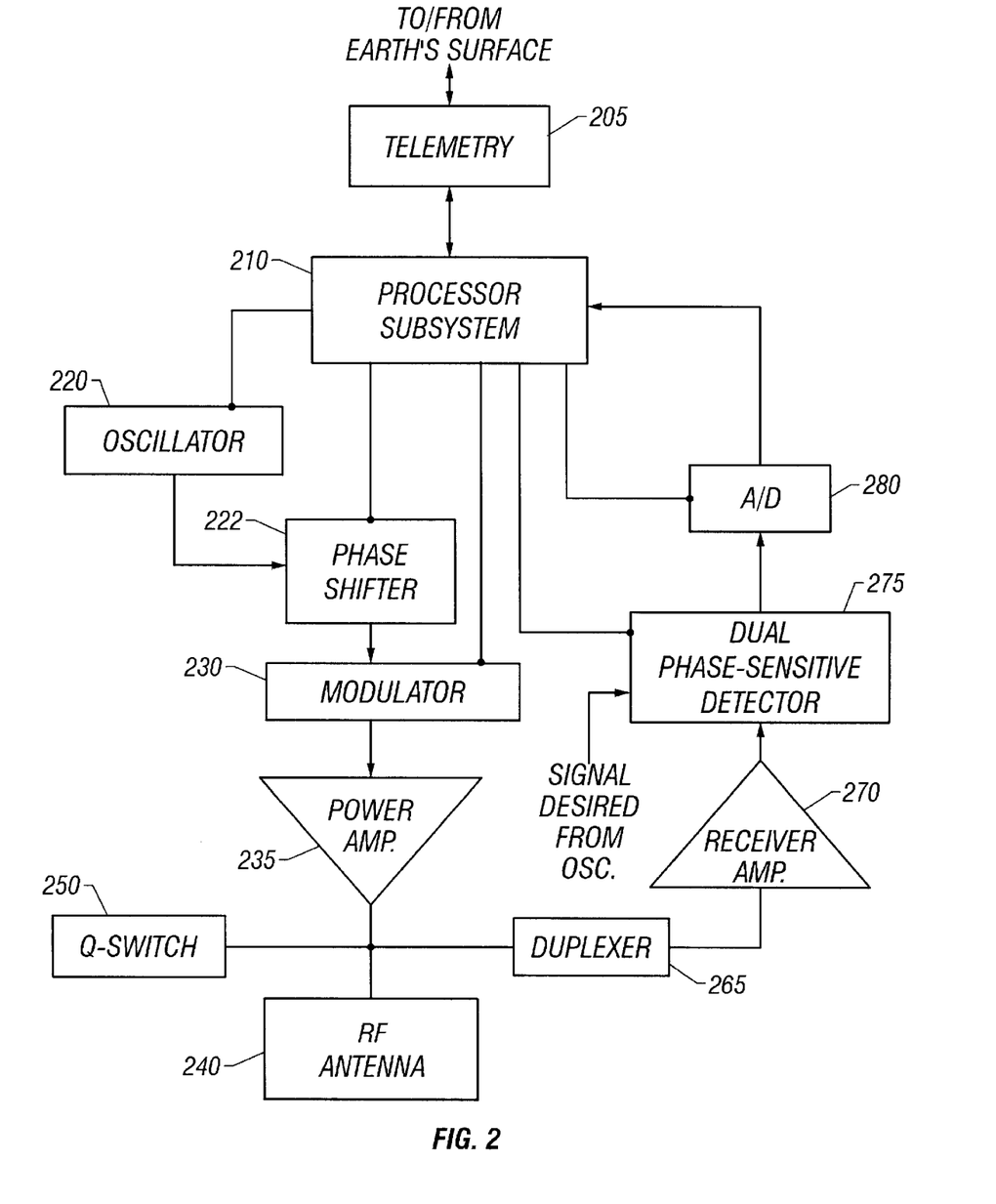
FIG. 2 is a block diagram of circuitry that can be utilized in conjunction with embodiments of the invention such as in the FIG. 1 embodiment.

FIG. 2 shows, in simplified form, circuitry of the general type set forth in U.S. Pat. No. 5,055,788 for producing the RF pulses and for receiving and processing the spin echoes. Reference can be made to said Patent for further detail.

Still referring to FIG. 2, the downhole processor subsystem is represented at 210. The processor subsystem 210 has associated memory, timing, interfaces, and peripherals (not separately shown), as is well known in the art. The processor subsystem is conventionally coupled with telemetry circuitry 205, for communication with the earth's surface. An oscillator 220 produces radio frequency (RF) signals at the desired resonant frequency or frequencies, and the output of the oscillator is coupled to a phase shifter 222 and then to a modulator 230, both of which are under control of the processor subsystem 210. The phase shifter and modulator can be controlled, in a manner known in the art, to produce the desired pulses of RF field, for example the 90 degree and 180 degree pulses utilized in embodiments hereof. As described, for example, in the U.S. Pat. No. 5,055,788, the oscillator 220 can be a plurality of oscillators used in a manner that facilitates the generation and ultimate detection of the desired signals. The output of modulator 230 is coupled, via a power amplifier 235, to the RF antenna 240. A Q-switch 250 can be provided to critically damp the RF antenna system to reduce antenna ringing. The antenna 240 is also coupled with a receiver section via duplexer 265, the output of which is coupled to receiver amplifier 270. The duplexer 265 protects the receiver amplifier 270 from the high power pulses which pass to the RF antenna 240 during the transmitting and damping modes. During the receiving mode, the duplexer 265 is effectively just a low impedance connection from the antenna to the receiver amplifier 270. The output of the receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal.

Although the logging device or tool 30 is shown as a single body, it may alternatively comprise separate components, and the tool may be combinable with other logging tools. Also, while a wireline is illustrated, alternative forms of physical support and communicating link can be used, for example in a measurement while drilling system.

Figure 3:
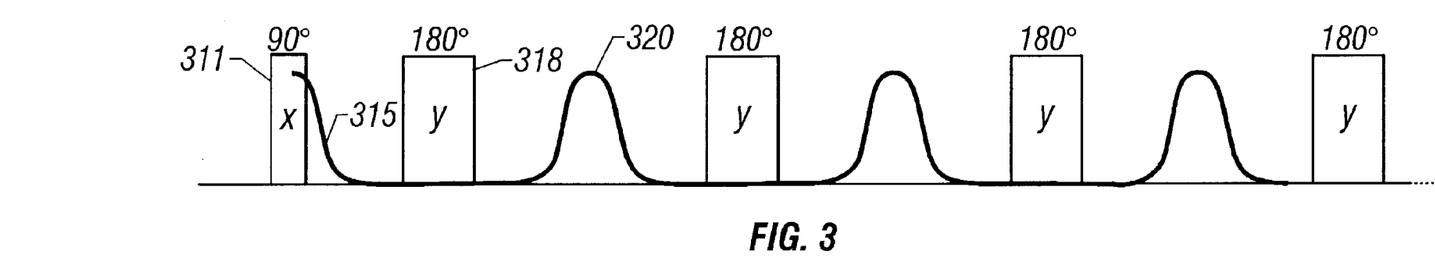
FIG. 3 is a diagram of a CPMG pulse sequence.

FIG. 3 illustrates an example of a CPMG sequence. [It can be noted that the principles hereof are not limited to improving ringing immunity in CPMG types of pulse sequences.] After appropriate prepolarization with the static field, a $90_x$ RF excitation pulse 311 is applied. The free induction decay is illustrated at 315. After a time τ, a $180_y$ RF refocusing pulse 318 is applied, and a spin echo 320 is acquired at approximately 2τ. The sequence of applied refocusing pulses and acquired spin echoes is then repeated many times in a typical NMR logging application. The spin echoes can be conventionally processed to obtain, for example, distribution of $T_2$'s, porosity, and/or other formation characteristics.

Figure 4:
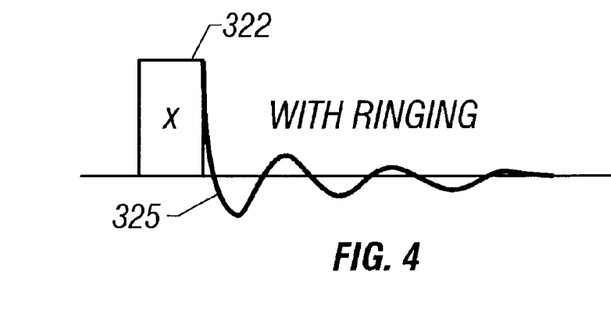
FIG. 4 is a graph that illustrates the type of acoustic ringing that results from RF pulses of the type used in a CPMG pulse sequence.
Figure 5:
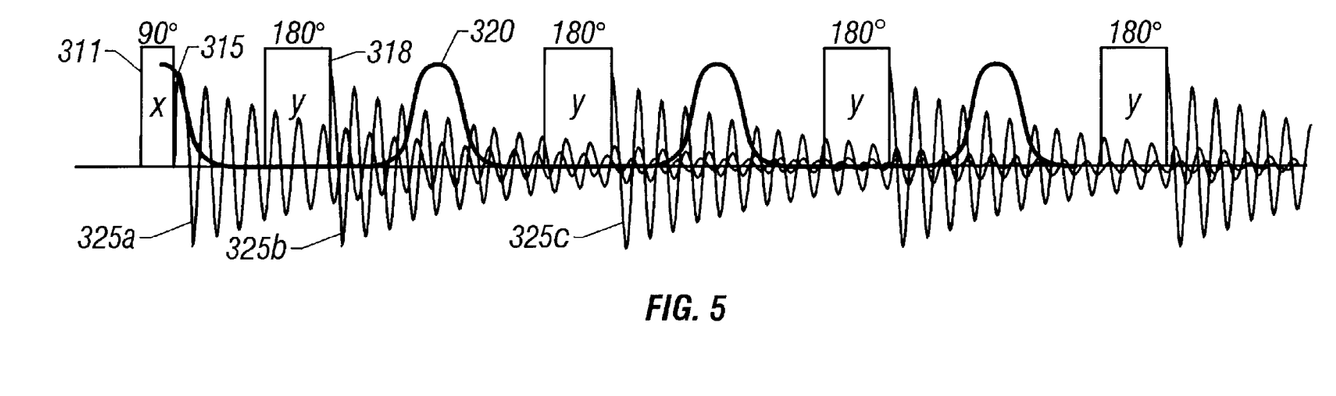
FIG. 5 is a graph of the CPMG pulse sequence of FIG. 3, with an illustration of acoustic ringing superimposed thereon.
Figure 6A:
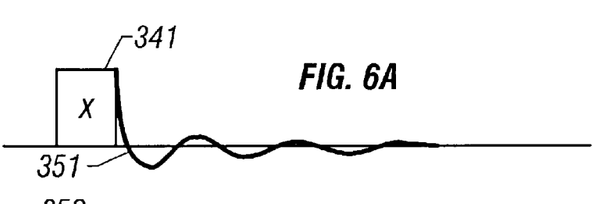
FIGS. 6A and 6B respectively show a positive-going and a negative-going RF pulse and the type of phase coherent acoustic ringing that results therefrom. These Figures use the same representation for +x and +y pulses (positive going) and use the same representation for −x and −y pulses (negative going). This simplification is for ease of illustration.
Figure 6B:
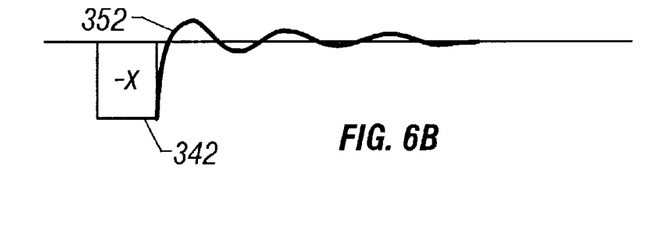

FIG. 4 is a simplified illustration of the type of acoustic ringing that can result from the RF pulses such as those of FIG. 3. The pulse 322 results in acoustic ringing 325 which can be represented as a damped oscillation. The diagram of FIG. 5 shows the pulse sequence and echoes as in FIG. 3, but includes the ringing from each pulse (labeled 325a, 325b, 325c), which is part of the total signal seen by the receiver being used to detect the spin echoes and can have a deleterious effect on the detection process. The diagram, of FIGS. 6A and 6B respectively show the ringing (labeled 351 and 352) that results from pulses 341 and 342 of opposite polarity, i.e., the carrier phases of the two pulses are separated by 180 degrees. It is seen that the ringing is phase coherent with the RF pulse; that is, it follows the phase of the RF pulse. Therefore, it cannot be averaged out by techniques such as stacking that are used to reduce incoherent noise.

Figure 7:
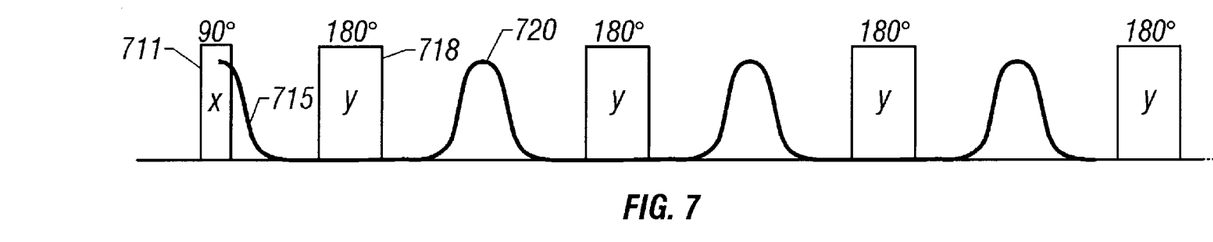
FIG. 7 is a diagram of a first cycle of a phase alternated pair pulse sequence.
Figure 8:
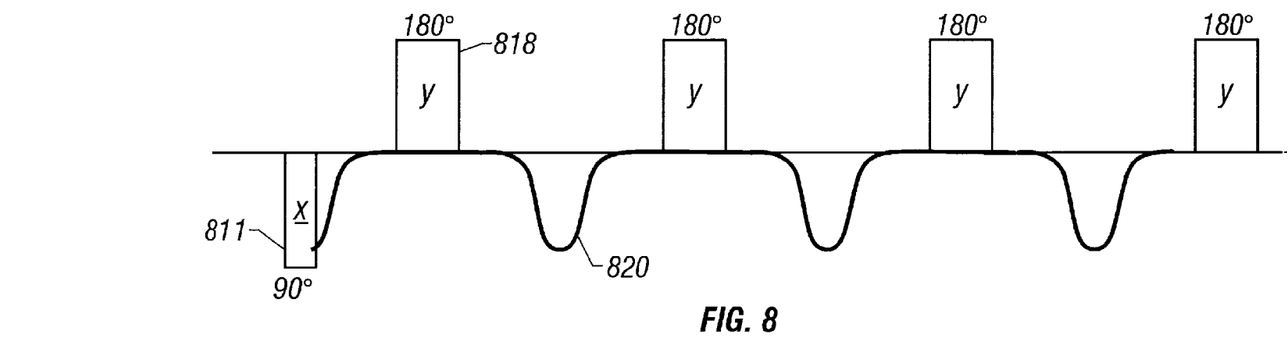
FIG. 8 is a diagram of a second cycle of a phase alternated pair pulse sequence. For purposes of clarity, the acoustic ringing is not shown.
Figure 9:
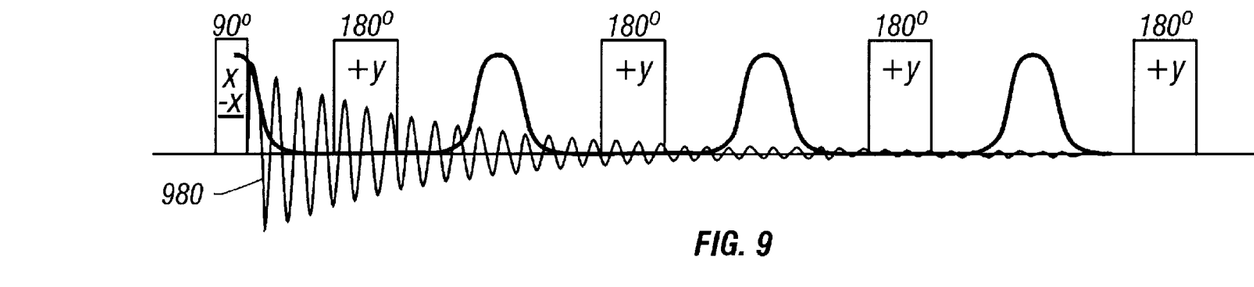
FIG. 9 is a diagram of a sum of the first and second cycles of the phase alternated pair sequence, showing how the ringing from 180 degree pulses is eliminated but the phase coherent acoustic ringing from the 90 degree pulses adds in phase, and its phase relationship with the echoes.

FIGS. 7, 8, and 9 show an example of known variation of CPMG, called "phase alternated pair", or "PAP", which has certain operational advantages, including the elimination of ringing from the 180 degree pulses. The PAP includes two pulse sequence cycles. The first of the pulse sequence cycles is illustrated in FIG. 7, which is similar to the pulse sequence of FIG. 3. In this case, the $90_x$ RF pulse is represented at 711, the free induction decay is represented at 715, the first $180_y$ pulse is represented at 718, the first spin echo is represented at 720, and the subsequent $180_y$ pulses and spin echoes are again unlabeled. The second pulse sequence cycle of the PAP is illustrated in FIG. 8. In this case, the phase of the excitation pulse is reversed compared to the sequence of FIG. 7. After the $90_{-x}$ excitation pulse 811, a $180_y$ refocusing pulse 818 is utilized, resulting in a spin echo 820 (with the usual repeating of refocusing and spin echoes). Two observations can be made. First, the 90 degree excitation pulse of FIG. 8 has opposite polarity from its counterpart in FIG. 7, causing the spin echoes (which are detected in the y direction) to have the opposite polarity. Second, as was noted above in conjunction with FIGS. 6A and 6B, the acoustic ringing is phase coherent, so the acoustic ringing from corresponding 180 degree pulses of the two pulse sequence cycles (of FIGS. 7 and 8) will have the same polarities. Therefore, the detected signals from the two pulse sequence cycles (of FIGS. 7 and 8) can be subtracted, and this will add the detected spin echo signals, but will substantially cancel the coherent ringing resulting from the 180 degree pulses. This is represented conceptually in the diagram of FIG. 9 which depicts the difference of the first pulse sequence cycle (of FIG. 7) and the second pulse sequence cycle (of FIG. 8). [The diagram of FIG. 9 is not to scale. The spin echoes add.] The FIG. 9 diagram also shows a limitation of the PAP technique; namely, that the acoustic ringing from the 90 degree pulses will add, and this ringing will tend to distort at least the first few spin echoes, often only the first spin echo, which can be a serious disadvantage in determining $T_2$ distributions and formation total porosity. In FIG. 9, the acoustic ringing from the 90 degree pulses is represented at 980. As shown, this ringing will be detected in conjunction with at least the first few spin echoes. In simplified equation form, the signals seen by the receiver for the pulse sequence first cycle (FIG. 7) can be represented as and the signal seen by the receiver for the pulse sequence second cycle (FIG. 8) can be represented as $$-R90+R180-ECHO. \qquad (2)$$

The difference of these signals is therefore $$2R90+2ECHO \qquad (3)$$

where R90 is the acoustic ringing from the 90 degree pulse, R180 is the acoustic ringing from the 180 degree pulses, and ECHO is a spin echo signal.

The ringing signal, in general, is caused by the superposition of many acoustic modes, and it decays according to $$R_{90}(t) = \sum_j A_j \exp[r_j t + i\omega_j t + \phi_j] \qquad (4)$$

where $A_j$ is the amplitude, $r_j$ is the damping rate, $\omega_j$ is the frequency, and $\Phi_j$ is the phase of j-th acoustic mode. The damping rate is found to be on the order of 100 Hz, which leads to ringing signals that last several milliseconds. Therefore, the 90° ringing signal mainly affects the intensity of the first few echoes as has been confirmed operationally.

In well logging, the first few echoes can be crucial for measuring short $T_2$ components and the total porosity. Therefore, it is preferable to suppress the ringing signal as much as possible. Substantial efforts have been made toward suppressing the ringing through hardware design (see e.g. U.S. Pat. No. 5,153,514). Although by careful hardware design one can minimize the ringing, it is difficult to completely eliminate this unwanted effect. This is especially true for logging tools which must be rugged and work under extreme environmental conditions of temperature, vibration, etc. in a confining borehole.

Figure 10:
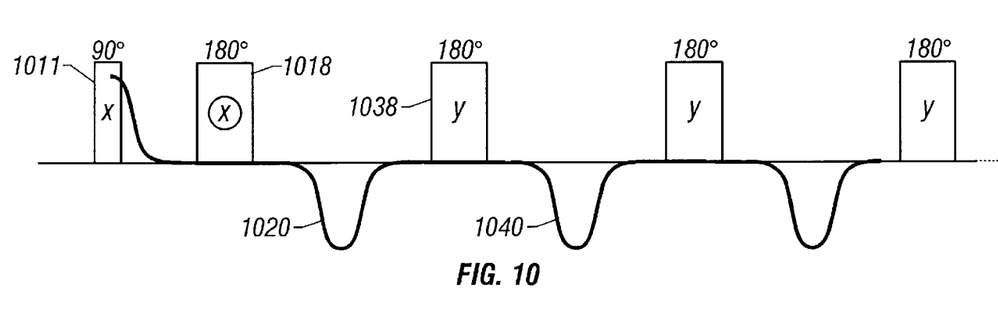
FIG. 10 is a diagram of a third cycle of a pulse sequence that is utilized in an embodiment of the invention.
Figure 11:
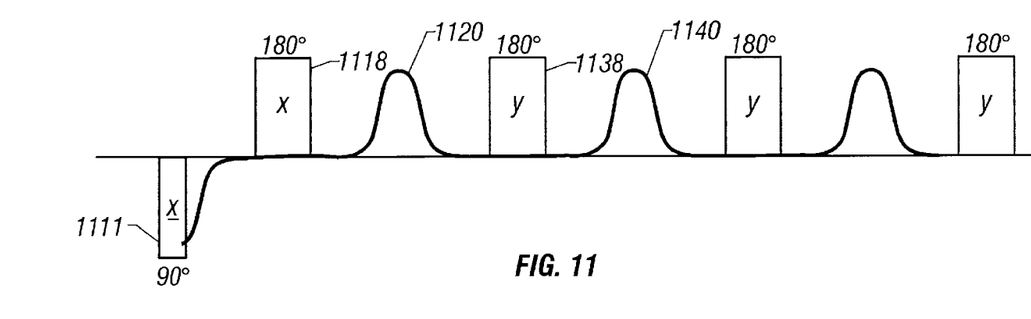
FIG. 11 is a diagram of a fourth cycle of a pulse sequence that is utilized in an embodiment of the invention.

In an embodiment of the invention, the PAP pulse sequence cycles can be followed by (or preceded by—the order of the individual pulse sequences being non-critical) two more pulse sequence cycles that are designed to provide detected signals that again will include a sum of the ringing signals from the 90 degree pulses (that is, 2R90), but in which the echo polarity will be reversed with respect to the previous case (that is, to obtain the sum −2ECHO). [The cycles can also be split up. All four sequences can be freely rearranged.] Then, by subtracting this result from the previous result (of (3) above), the R90 components will subtract out and the ECHO components will add. This is illustrated in FIGS. 10–13. FIG. 10 shows the pulse sequence third cycle, which employs a $90_x$ excitation pulse 1011, and a $180_x$ refocusing pulse 1018. The first spin echo, which has a negative polarity, is labeled 1020. The next refocusing pulse is a $180_y$ pulse 1038, followed by another spin echo 1040 of negative polarity. [The subsequent $180_y$ pulses and spin echoes are repeated but are not labeled.] FIG. 11 illustrates the fourth cycle for this embodiment. In this pulse sequence cycle, the $90_{-x}$ excitation pulse 1111 has opposite polarity to its counterpart in FIG. 10, followed by a first refocusing pulse 1118 that is a $180_x$ pulse. This is followed by a spin echo 1120 which is of a positive polarity. Then, a second refocusing pulse 1138, which is a $180_y$ pulse, is followed by another spin echo (1140) of positive polarity. [The subsequent $180_y$ pulses and spin echoes are not labeled.]

Figure 12:
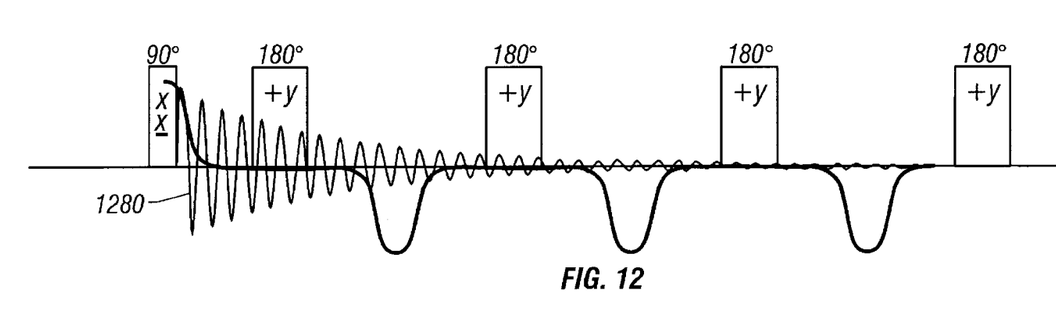
FIG. 12 is diagram of a sum of the third and fourth cycles of pulse sequence, showing how the phase coherent acoustic ringing from the 90 degree pulses adds in phase, and its phase relationship with the echoes.

Thus, it can be observed that by employing the pulse sequences of the third and fourth cycles (FIGS. 10 and 11, respectively) the 90° excitation pulses and the spin echoes all have opposite polarities, and the 180 degree pulses have the same polarities. Therefore, when the received signals from the third and fourth cycles of pulse sequences are subtracted, the acoustic ringing from the corresponding 180 degree pulses will substantially cancel, and the corresponding spin echoes will add. This is represented conceptually in FIG. 12 which depicts the sum of the third pulse sequence cycle (of FIG. 10) and the fourth pulse sequence cycle (of FIG. 11). [Again the diagram of FIG. 12 is not to scale. The negative polarity spin echoes add.] In the FIG. 12 diagram, the acoustic ringing from the 90 degree pulses adds to give ringing 1280. Again, it is seen that this ringing will be detected in conjunction with at least the first few spin echoes. In this case, in simplified equation form, the signals seen by the receiver for the pulse sequence of the third cycle (FIG. 10) can be represented as $$R90+R180-ECHO \qquad (5)$$

and the signals seen by the receiver for the pulse sequence of the fourth cycle (FIG. 11) can be represented as $$-R90+R180+ECHO. \qquad (6)$$

The difference of these signals is therefore $$2R90-2ECHO \qquad (7)$$

where, again, R90 is the acoustic ringing from the 90 degree pulse, R180 is the acoustic ringing from the 180 degree pulses, and ECHO is a spin echo signal.

Figure 13:
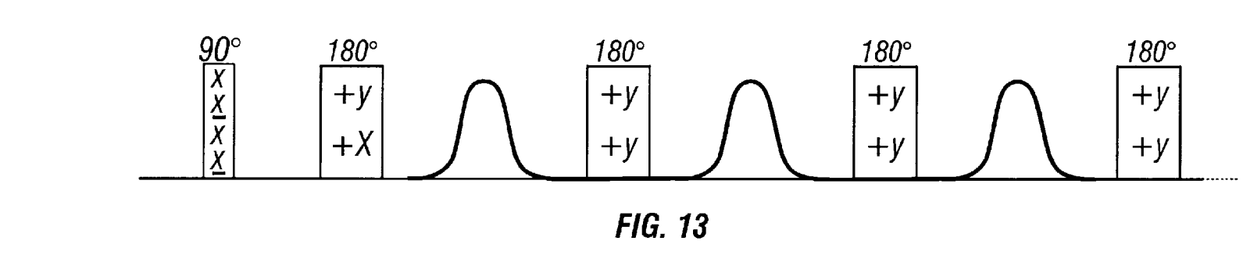
FIG. 13 is a diagram representing the difference of two pairs of cycles of the received corresponding echoes of the four cycles of pulse sequences in accordance with an embodiment of the invention and is also useful in illustrating how the phase coherent acoustic ringing from the 90 degree and 180 degree pulses is cancelled.

FIG. 13 is a conceptual representation of the results of subtracting the received signals represented in expression (7) [that is, the sum of the third and fourth cycles of pulse sequences] from the received signals represented in expression (3) [that is, the sum of the first and second cycles of pulse sequences]. The ringing from the 90 degree pulses will subtract, and the spin echo signals will add. [The ringing from the 180 degree pulses was already removed from each of the sums represented by expressions (7) and (3), respectively, as previously described.] This can also be demonstrated directly from the subtraction of expression (7) from expression (3), as follows:

$$(2R90 + 2ECHO)-(2R90-2ECHO)=4ECHO \qquad (8)$$

Thus, as expression (8) shows, this embodiment of the invention uses four phase cycles to eliminate the acoustic ringing caused by both the excitation and by refocusing pulses. In general, the pulse sequences in the four phase cycle of the present embodiment should preferably fulfill the requirements to be summarized momentarily. Although in the description so far the phases of the pulses are limited to the standard orthogonal phases x, y, −x, −y, an aspect hereof is that there is a set relationship between the phases of the refocusing pulses, and the relationship is not limited to the above indicated four phases. [The phase of the excitation pulse is called $\phi 0$. The choice of this phase is arbitrary, so for the following $\phi 0=0$ deg. All phases are understood to be relative to $\phi 0$.] The requirements for this embodiment are as follows: (1) Ringing from the first refocusing pulse is eliminated within a pair of sequences by inverting the phase of the excitation pulse with respect to the phase of the first refocusing pulse (i.e., changing their phase difference by 180 degrees) from one sequence to the other (PAP). This relationship is used between FIGS. 7 and 8 and also between FIGS. 10 and 11. (2) Ringing from the remaining refocusing pulses is either eliminated as described under requirement (1) or by inverting the phase of the remaining refocusing pulses between sequences with the same $\phi 0$ and different $\phi 1$.

The above example uses the first approach. (3) Ringing from the excitation pulse is eliminated within a pair of sequences by shifting the phase, $\phi 1a$, of the first refocusing pulse in one sequence by +90 degrees or −90 degrees with respect to the phase of the first refocusing pulse, $\phi 1b$, in the other sequence. This relationship is used between FIGS. 7 and 10 and also between FIGS. 8 and 11. The Figures show the special case of requirement (3) that can be implemented: $\phi 1a=0$ deg or 180 deg for one sequence and $\phi 1b=90$ deg or −90 deg for the other. The remaining refocusing pulses in a sequence are identical. (4) For optimal flip angle and off resonance error correction, the phase $\phi 2$ of the remaining refocusing pulses is chosen to be the same as or opposite to the phases of the echoes, i.e. $\phi 2=90$ deg$-2\phi 1a$ or 270 deg$-2\phi 1a$ (which, for the above special case becomes $\phi 2=+90$ deg or −90 deg). Both choices can be present in the phase cycle as long as their ringing is eliminated after the phase cycle (see requirement (2)). To correct hardware imperfections (receiver DC offset) a further requirement is: (5) The phases of the excitation pulses from one sequence to the other should be chosen such that the echoes in the two pairs of echo trains have opposite phase, e.g., echoes in FIGS. 7 and 11 have a phase of +90 deg and echoes in FIGS. 8 and 10 have a phase of −90 deg.

Examples of four cycles of pulse sequences for the present embodiment are as follows:

$$x[y]^{n+1}, \underline{x}[y]^{n+1}, xx[y]^n, \underline{xx}[y]^n,$$

$$x[\underline{y}]^{n+1}, \underline{x}[\underline{y}]^{n+1}, xx[y]^n, \underline{xx}[y]^n$$

$$x[\underline{y}]^{n+1}, \underline{x}[\underline{y}]^{n+1}, xx[y]^n, \underline{xx}[y]^n$$

$$x[y]^{n+1}, \underline{x}[y]^{n+1}, xx[y]^n, \underline{xx}[y]^n$$

$$x[y]^{n+1}, \underline{x}[y]^{n+1}, xx[\underline{y}]^n, \underline{xx}[\underline{y}]^n$$

$$x[\underline{y}]^{n+1}, \underline{x}[\underline{y}]^{n+1}, xx[\underline{y}]^n, \underline{xx}[\underline{y}]^n$$

$$x[\underline{y}]^{n+1}, \underline{x}[\underline{y}]^{n+1}, xx[\underline{y}]^n, \underline{xx}[\underline{y}]^n$$

$$x[y]^{n+1}, \underline{x}[y]^{n+1}, xx[\underline{y}]^n, \underline{xx}[\underline{y}]^n$$

$$x[y]^{n+1}, \underline{x}[\underline{y}]^{n+1}, xx[y]^n, xx[\underline{y}]^n$$

$$x[y]^{n+1}, x[\underline{y}]^{n+1}, xx[\underline{y}]^n, xx[y]^n$$

Phases do not have to be fixed to the four orthogonal phases x, y, $\underline{x}$, and $\underline{y}$. A general form is:

$$\phi 0a\phi 1a[\phi 2i]^n, \phi 0a\phi 1b[\phi 2j]^n, -\phi 0b\phi 1a[\phi 2k]^n, -\phi 0b\phi 1b[\phi 21]^n$$

where $\phi 2i=\phi 2j=\phi 2k=\phi 2l=\phi 2a$
or $\phi 2i=\phi 2j=\phi 2k=\phi 2l=\phi 2b$
or $\phi 2i=\phi 2j=\phi 2a$ and $\phi 2k=\phi 2l=\phi 2b$
or $\phi 2i=\phi 2j=\phi 2b$ and $\phi 2k=\phi 2l=\phi 2a$
or $\phi 2i=\phi 2k=\phi 2a$ and $\phi 2j=\phi 2l=\phi 2b$
or $\phi 2i=\phi 2k=\phi 2b$ and $\phi 2j=\phi 2l=\phi 2a$
with
$\phi 0a=\phi 0$
$\phi 0b=\phi 0+180°$
$\phi 1b=\phi 1a+90°$
$\phi 1b=\phi 1a-90°$
$\phi 2a=\phi 0-90°-2\phi 1a$
$\phi 2b=\phi 2a+180°$ Examples of a covered four phase cycle are:

$0°45°[0°]^n, 180°45°[0°]^n, 0°-45°[0°]^n, 180°-45°[0°]^n$ $0°45°[180°]^n, 180°45°[180°]^n, 0°-45°[180°]^n, 180°-45°[180°]^n$ $0°45°[0°]^n, 180°45°[0°]^n, 0°-45°[180°]^n, 180°-45°[180°]^n$ $0°45°[180°]^n, 180°45°[180°]^n, 0°-45°[0°]^n, 180°-45°[0°]^n$ $0°45°[0°]^n, 180°45°[180°]^n, 0°-45°[0°]^n, 180°-45°[180°]^n$ $0°45°[180°]^n, 180°45°[0°]^n, 0°-45°[180°]^n, 180°-45°[0°]^n.$

It can be noted that the order of the sequences is arbitrary. Only the relative pulse phases in the cycle are important, because the definition of which phase is called x and the choice of $\phi 0$ is arbitrary.

A first embodiment for eliminating ringing with a four cycle pulse sequence was initially described above. Another approach, which also employs a four-phase cycling sequence, again uses a PAP as the first two cycles. [As before, the order of the individual cycles is not critical.] In the remaining two sequences of this embodiment, a 180° inverting pulse is applied before the first 90° pulse so the magnetization rotates to the −z direction. After the magnetization stays on −z axis for a length of time $\tau'$, it is rotated to the y-axis by applying a 90°$\times$pulse, followed by 180°$_y$ refocusing pulses as is standard in CPMG pulse sequencing. This results in a signal, seen by the receiver that is represented as $$R180_x+R90+R180_y-ECHO \qquad (9)$$

Equation (9) has the same terms (some with different signs) as equation (1) except for the extra $R180_x$ term. To eliminate this term, the phase of the first 90° pulse in the fourth cycle pulse sequence can be inverted to obtain $$R180_x-R90+R180_y+ECHO \qquad (10)$$

Subtracting (10) from (9) gives $$2R90-2ECHO. \qquad (11)$$

The similarity of equations (11) and (7) can be noted. Since the ringing response is considered to be linear, subtracting (11) from (3) results in $$(2R90+2ECHO)-(2R90-2ECHO)=4ECHO. \qquad (12)$$

Equation (12) shows that the 90° as well as the 180° ringing signals are suppressed by combining the four-phase cycles of this second embodiment. The technique of this second embodiment is illustrated graphically in FIG. 14.

Figure 14:
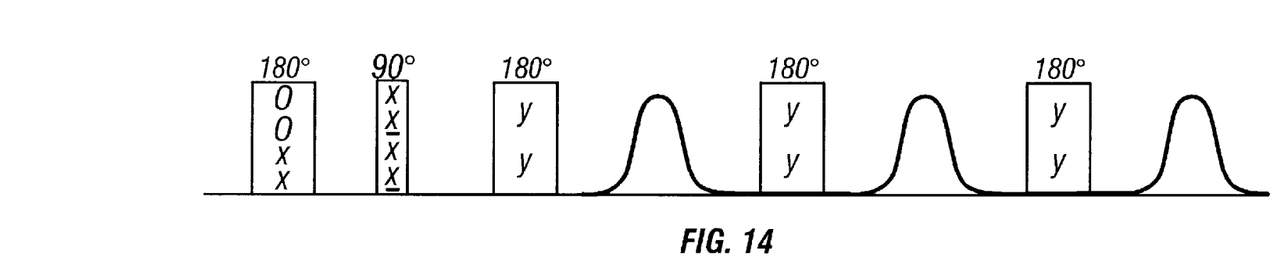
FIG. 14 is a pulse sequence diagram illustrating operation of a further embodiment of the invention.

The time delay between the inverting (180) pulse and the first excitation pulse, $\tau'$, can be varied depending on the particular application. Normally, $\tau'$is taken to be long enough to allow the ringing due to the 180 pulse to decay below some acceptable limit, and particularly to allow the receiver electronics to recover, before the first echo detection. In the limit when $\tau'=0$, the 180 and the 90 pulses add together, forming a composite 270 pulse. This is a special case of the second embodiment, where the excitation pulses for the first pair of sequences are 90, while the second two pair of sequences are excited by 270 pulses, and it appears as if there are no separate inverting pulses.

Figure 15:
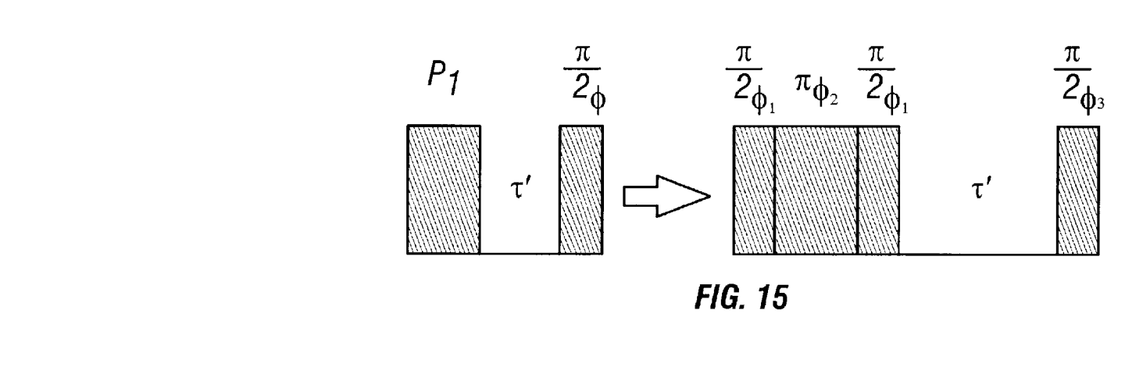
FIG. 15 is a pulse sequence diagram illustrating operation of a variation of the further embodiment of the invention.

An alternative way of viewing the described second embodiment is to consider the initial 180° pulse as the sum of two 90° pulses. The phases of the two 90° pulses do not have to be the same, making the resulting pulse a composite pulse. In the first two cycles of this variation, the phases of the two 90° pulses are opposite, adding to zero. In the third and fourth cycles, the phases are the same, adding to a 180° pulse. Further, one can replace the first 90° pulse in standard CPMG sequence with a composite excitation pulse such as the one shown in FIG. 15, namely $90_{\phi_1}-90_{\phi_2}-\tau'-90_{\phi_3}$. If $\phi_1=-\phi_2$, the two 90° pulses cancel each other and the third 90° pulse will initiate a normal CPMG sequence. On the other hand if $\phi_1$ and $\phi_2$ add together, the net result is a 180° pulse in addition to the standard 90° pulse and the last two sequences of originally described second embodiment are formed. An advantage of composite pulse approach, is that it can be readily generalized to more complicated pulse shapes.

Figure 16:
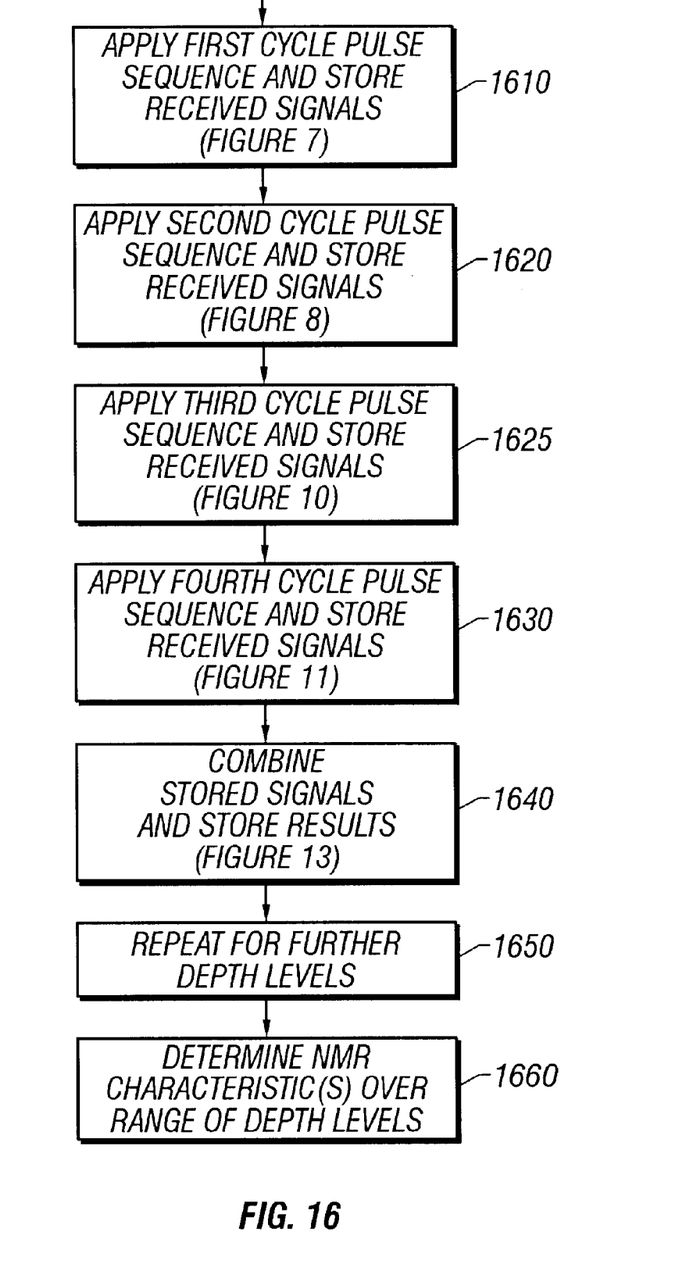
FIG. 16 is a flow diagram of a routine for controlling a processor for practising an embodiment of the invention.
Figure 17:
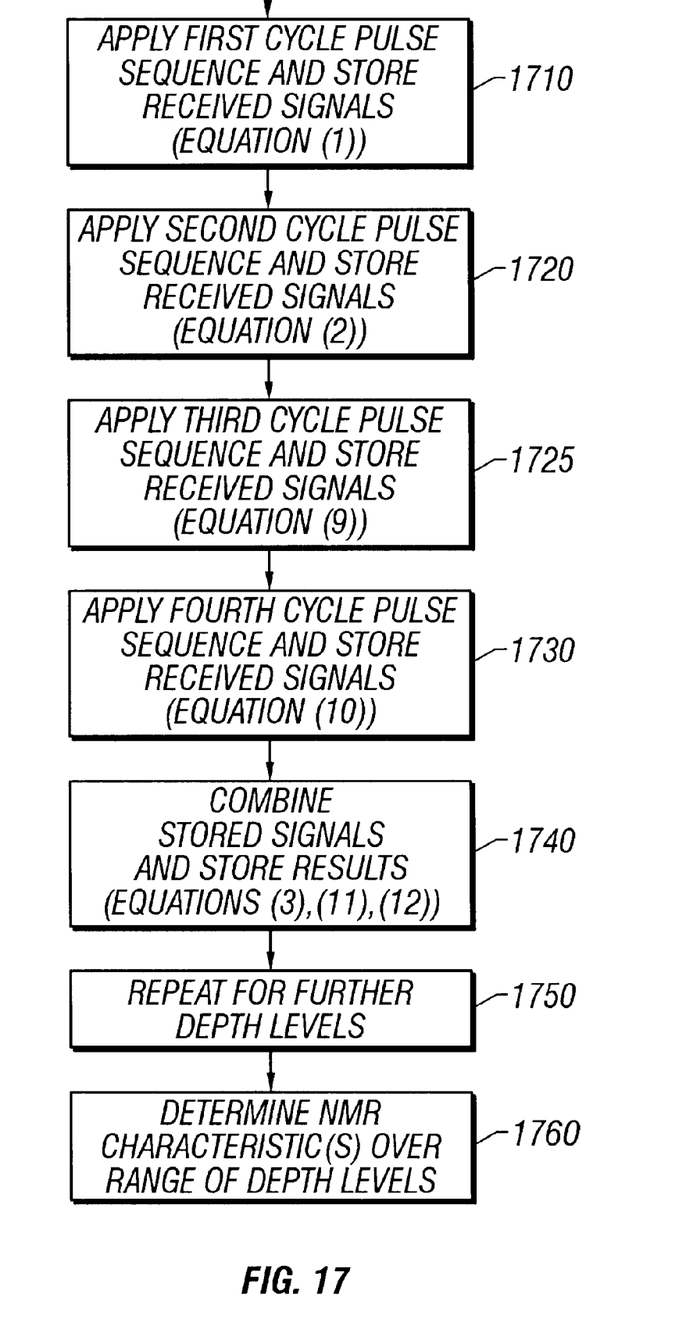
FIG. 17 is a flow diagram of a routine for controlling a processor for practising a further embodiment of the invention.

Referring to FIGS. 16 and 17, there are shown flow diagrams of a routine for controlling a processor in accordance with embodiments of the invention. The processor can be the downhole processor, the uphole processor, or a remote processor which operates subsequently on stored and/or transmitted log-representative signals, as well as combinations of downhole, uphole, and remote processors.

In FIG. 16, the block 1610 represents applying of the first cycle pulse sequence as in FIG. 7, and the storage of the received signals. The block 1620 represents applying of the second cycle pulse sequence as in FIG. 8, and the storage of the received signals. The block 1625 represents applying the third cycle pulse sequence as in FIG. 10, and the storage of the received signals. Then, the block 1630 represents applying the fourth cycle pulse sequence as in FIG. 11, and the storage of the received signals. As previously noted, the order in which the individual cycles are applied is not critical. Next, the block 1640 represents the combining of the stored signals and the storage of the results, as in FIG. 13. The procedure can be repeated for further depth levels, as represented by the block 1650, and NMR characteristics can be determined, over the range of depth levels, from the received and processed NMR signals, as is well known in the art. It will be understood that, in this procedure, as well as in the flow diagram of FIG. 17, the order in which some of the operations is performed can be varied. For example, the signal combinations of block 1640 can be performed after data is taken and stored over the range of depth levels, or computations in accordance with block 1660 can be implemented for individual depth levels, if desired, before data is taken for other depth levels.

The flow diagram of FIG. 17 is generally similar to the flow diagram of FIG. 16, except that the second embodiment of the invention is implemented thereby. More specifically, the block 1710 represents applying of the first cycle pulse sequence, as in equation (1), and storing the received signals. The block 1720 represents applying of the second cycle pulse sequence, as in equation (2), and storing the received signals. The block 1725 represents applying of the third cycle pulse sequence, as in equation (9), and storing the received signals. Then, the block 1730 represents applying of the fourth cycle pulse sequence, as in equation (10), and storing the received signals. Again, the order in which the individual cycles are applied is not critical. The stored signals can then be combined, in accordance with equations (3), (11), and (12), and the results stored, as represented by the block 1740. The technique can be repeated for further depth levels (block 1750), and NMR characteristics can be determined over the range of depth levels (block 1760), as before.

The invention has been described with reference to particular preferred embodiments, but variations within the spirit and scope of the invention will occur to those skilled in the art. For example, it will be understood that other orders and types of pulse sequences, which are consistent with the principles set forth, can be utilized.

What is claimed is:

1. A method for obtaining nuclear magnetic resonance measurements from formations surrounding an earth borehole, comprising the steps of:
   providing a logging device that is moveable through the borehole and through formations in which a static magnetic field is present;
   producing, from said logging device, a series of cycles of pulse sequences in the formations, each of said pulse sequences including at least an RF excitation pulse and several RF refocusing pulses, the series of pulse sequences including at least one modified pulse sequence having at least one modified pulse;
   receiving, at said logging device, spin echoes from the formations to produce spin echo signals that may include spurious ringing signals from the excitation and refocusing pulses, wherein the modified pulse causes a shift of a spin echo polarity for the spin echoes associated with the modified pulse sequence relative to the polarity of spurious ringing signals from the excitation pulse associated with the modified pulse sequence; and
   combining spin echo signals from corresponding spin echoes of each of said cycles of pulse sequences to obtain combined spin echo signals in which spurious ringing from the excitation pulses and refocusing pulses of said pulse sequences is substantially canceled.

2. The method as defined by claim 1, wherein said step of providing a logging device that is moveable through the borehole and through formations in which a static magnetic field is present includes producing, form said logging device, a static magnetic field in the formations.

3. The method as defined by claim 1, wherein said static magnetic field is earth's magnetic field.

4. The method as defined by claim 1, wherein said step of producing a series of cycles of pulse sequences in the formations further includes producing an RF inverting pulse in some of said cycles of pulse sequences, and wherein said step of receiving spin echoes from the formations to produce spin echo signals includes receiving spin echoes to produce spin echo signals that may includes spurious ringing signals from the inverting pulses, and wherein said combining step includes combining spin echoes of each of said cycles of pulse sequences to obtain combined spin echoes in which spurious ringing from the inverting pulses of the pulse sequences is substantially cancelled.

5. The method as defined by claim 1, wherein said steps of producing said cycles of pulse sequences and combining spin echo signals include inverting phases of corresponding and refocusing pulses in each of said series of cyclesto obtain said substantial cancellation of said spurious ringing from the excitation and refocusing pulses.

6. The method as defined by claim 4, wherein said steps of producing said cycles of pulse sequence and combining spin echo signals includes inverting phases of corresponding excitation, refocusing, and inverting pulses in each of said cycles to obtain said substantial cancellation of said spurious ringing from the excitation, refocusing and inverting pulses.

7. The method as defined by claim 1, wherein said series of cycles of pulse sequences comprises four cycles of pulse sequences.

8. The method as defined by claim 5, wherein said series of cycles of pulse sequences comprises four cycles of pulse sequences.

9. The method as defined by claim 6, wherein said series of cycles of pulse sequences comprises four cycles of pulse sequences.

10. The method as defined by claim 7, wherein said step of combining spin echo signals from corresponding spin echoes of each of said cycles of pulse sequences to obtain combined spin echo signals comprises combining corresponding spin echo signals from two of said cycles and subtracting the spin echo signals from the other two of said cycles.

11. The method as defined by claim 8, wherein said step of combining spin echo signals from corresponding spin echoes of each of said cycles of pulse sequences to obtain combined spin echo signals comprises combining corresponding spin echo signals from two of said cycles and subtracting the spin echo signals from the other two of said cycles.

12. The method as defined by claim 7, wherein all the spin echo signals of two of the four cycles have a polarity that is opposite to that of all the spin echo signals of the other two of the four cycles.

13. The method as defined by claim 7, wherein all the spin echo signals of two of the four cycles have a polarity that is opposite to that of all the spin echo signals of the other two of the four cycles.

14. The method as defined by claim 1, wherein said excitation pulses are 90 degree pulses and said refocusing pulses are 180 degree pulses.

15. The method as defined by claim 7, wherein said excitation pulses are 90 degree pulses and said refocusing pulses are 180 degree pulses.

16. The method as defined by claim 6, wherein said excitation pulses are 90 degree pulses and said refocusing and inverting pulses are 180 degree pulses.

17. The method as defined by claim 9, wherein said excitation pulses are 90 degree pulses and said refocusing and inverting pulses are 180 degree pulses.

18. The method as defined by claim 9, wherein two of the four cycles include an inverting pulse before the excitation pulse.

19. The method as defined by claim 9, wherein two of the four cycles include an inverting pulse that is divided into a plurality of pulses.

20. The method as defined by claim 18, wherein said excitation and inverting pulses are combined into a single pulse in each of a plurality of said pulse sequences.

21. The method as defined by claim 20, wherein each of said combined single pulses is a 270 degree pulse.

22. The method as defined by claim 7, wherein said combined spin echo signal is derived from a combination selected from a group consisting of the following combinations:

$x[y]^{n+1}$, $\underline{x}[y]^{n+1}$, $xx[y]^n$, $\underline{xx}[y]^n$,
$x[\underline{y}]^{n+1}$, $\underline{x}[\underline{y}]^{n+1}$, $xx[y]^n$, $\underline{xx}[y]^n$
$x[y]^{n+1}$, $\underline{x}[y]^{n+1}$, $x\underline{x}[y]^n$, $\underline{xx}[y]^n$
$x[y]^{n+1}$, $\underline{x}[y]^{n+1}$, $xx[y]^n$, $\underline{xx}[y]^n$
$x[y]^{n+1}$, $\underline{x}[y]^{n+1}$, $xx[\underline{y}]^n$, $\underline{xx}[\underline{y}]^n$
$x[y]^{n+1}$, $\underline{x}[y]^{n+1}$, $x\underline{x}[\underline{y}]^n$, $\underline{xx}[\underline{y}]^n$
$x[y]^{n+1}$, $\underline{x}[y]^{n+1}$, $x\underline{x}[\underline{y}]^n$, $xx[\underline{y}]^n$
$x[y]^{n+1}$, $\underline{x}[\underline{y}]^{n+1}$, $x\underline{x}[\underline{y}]^n$, $xx[\underline{y}]^n$
$x[y]^{n+1}$, $\underline{x}[\underline{y}]^{n+1}$, $x\underline{x}[y]^n$, $xx[\underline{y}]^n$
$x[y]^{n+1}$, $\underline{x}[\underline{y}]^{n+1}$, $x\underline{x}[\underline{y}]^n$, $xx[y]^n$.

23. The method as defined by claim 8, wherein said combined spin echo signal is derived from a combination selected from a group consisting of the following combinations:

$x[y]^{n+1}$, $\underline{x}[y]^{n+1}$, $x\underline{x}[y]^n$, $\underline{xx}[y]^n$,
$x[\underline{y}]^{n+1}$, $\underline{x}[\underline{y}]^{n+1}$, $xx[y]^n$, $\underline{xx}[y]^n$
$x[y]^{n+1}$, $\underline{x}[y]^{n+1}$, $x\underline{x}[y]^n$, $\underline{xx}[y]^n$
$x[y]^{n+1}$, $\underline{x}[y]^{n+1}$, $x\underline{x}[y]^n$, $\underline{xx}[y]^n$
$x[y]^{n+1}$, $\underline{x}[y]^{n+1}$, $x\underline{x}[y]^n$, $\underline{xx}[y]^n$
$x[y]^{n+1}$, $\underline{x}[y]^{n+1}$, $x\underline{x}[y]^n$, $\underline{xx}[y]^n$
$x[y]^{n+1}$, $\underline{x}[y]^{n+1}$, $x\underline{x}[y]^n$, $\underline{xx}[y]^n$
$x[y]^{n+1}$, $\underline{x}[\underline{y}]^{n+1}$, $x\underline{x}[y]^n$, $xx[\underline{y}]^n$
$x[y]^{n+1}$, $\underline{x}[\underline{y}]^{n+1}$, $x\underline{x}[y]^n$, $xx[\underline{y}]^n$.

24. The method as defined by claim 7, wherein said combined spin echo signal is derived from a combination selected from a group consisting of the following combinations:

$0°45°[0°]^n$, $180°45°[0°]^n$, $0°-45°[0°]^n$, $180°-45°[0°]^n$ $0°45°[180°]^n$, $180°45°[180°]^n$, $0°-45°[180°]^n$, $180°-45°[180°]^n$ $0°45°[0°]^n$, $180°45°[0°]^n$, $0°-45°[180°]^n$, $180°-45°[180°]^n$ $0°45°[180°]^n$, $180°45°[180°]^n$, $0°-45°[0°]^n$, $180°-45°[0°]^n$ $0°45°[0°]^n$, $180°45°[180°]^n$, $0°-45°[0°]^n$, $180°-45°[180°]^n$ $0°45°[180°]^n$, $180°45°[0°]^n$, $0°-45°[180°]^n$, $180°-45°[0°]^n$.

25. The method as defined by claim 8, wherein said combined spin echo signal is derived from a combination selected from a group consisting of the following combinations:

$0°45°[0°]^n$, $180°45°[0°]^n$, $0°-45°[0°]^n$, $180°-45°[0°]^n$ $0°45°[180°]^n$, $180°45°[180°]^n$, $0°-45°[180°]^n$, $180°-45°[180°]^n$ $0°45°[0°]^n$, $180°45°[0°]^n$, $0°-45°[180°]^n$, $180°-45°[180°]^n$ $0°45°[180°]^n$, $180°45°[180°]^n$, $0°-45°[0°]^n$, $180°-45°[0°]^n$ $0°45°[0°]^n$, $180°45°[180°]^n$, $0°-45°[0°]^n$, $180°-45°[180°]^n$ $0°45°[180°]^n$, $180°45°[0°]^n$, $0°-45°[180°]^n$, $180°-45°[0°]^n$.

26. The method as defined by claim 7, wherein said combined spin echo signal is derived from the following combination: $\phi 0a\phi 1a[\phi 2i]^n$, $\phi 0a\phi 1b[\phi 2j]^n$, $-\phi 0b\phi 1a[\phi 2k]^n$, $-\phi 0b\phi 1b[\phi 2l]^n$.

27. The method as defined by claim 8, wherein said combined spin echo signal is derived from the following combination: $\phi 0a\phi 1a[\phi 2i]^n$, $\phi 0a\phi 1b[\phi 2j]^n$, $-\phi 0b\phi 1a[\phi 2k]^n$, $-\phi 0b\phi 1b[\phi 2l]^n$.

28. The method as defined by claim 1, further comprising determining a nuclear magnetic resonance characteristic of said formations from said combined spin echo signals.

29. The method as defined by claim 1, wherein said step of providing a logging device that is moveable through the borehole includes providing a logging device suspended on a wireline.

30. The method as defined by claim 1, wherein said step of providing a logging device that is moveable through the borehole includes providing a logging device that is mounted on a drill string.

31. Apparatus for obtaining nuclear magnetic resonance measurements from formations surrounding an earth borehole, comprising:

a logging device that is moveable through the borehole;

means in said logging device for producing a static magnetic field in the formations;

means in said logging device for producing a series of cycles of pulse sequences in the formations, each of said pulse sequences including at least an RF excitation pulse and several RF refocusing pulses, the series of pulse sequences including at least one modified pulse sequence having at least one modified pulse;

means in said logging device for receiving spin echoes from the formations to produce spin echo signals that may include spurious ringing signals from the excitation and refocusing pulses, wherein the modified pulse causes a shift of a spin echo polarity for the spin echoes associated with the modified pulse sequence relative to the polarity of spurious ringing signals from the excitation pulse associated with the modified pulse sequence; and means for combining spin echo signals from corresponding spin echoes of each of said cycles of pulse sequences to obtain combined spin echo signals in which spurious ringing from the excitation pulses and refocusing pulses of said pulse sequences is substantially canceled.

32. The apparatus as defined by claim 31, wherein said means for producing said cycles of pulse sequences and combining spin echo signals includes means for inverting phases of corresponding excitation and refocusing pulses in each of said cycles to obtain said substantial cancellation of said spurious ringing from the excitation and refocusing pulses.

33. Apparatus as defined by claim 31, wherein said series of cycles of pulse sequences comprises four cycles of pulse sequences.

34. Apparatus as defined by claim 32, wherein said series of cycles of pulse sequences comprises four cycles of pulse sequences.

35. Apparatus as defined by claim 33, wherein said means for combining spin echo signals from corresponding spin echoes of each of said cycles of pulse sequences to obtain combined spin echo signals comprises means for combining corresponding spin echo signals from two of said cycles and subtracting the spin echo signals from the other two of said cycles.

36. Apparatus as defined by claim 31, wherein said excitation pulses are 90 degree pulses and said refocusing pulses are 180 degree pulses.

37. Apparatus as defined by claim 33, further comprising means for providing an inverting pulse before the excitation pulse in two of said four cycles.

38. A method for measuring nuclear magnetic resonance properties of an earth formation surrounding a wellbore, comprising:

inducing a plurality of sequences of pulsed, radio frequency magnetic fields in the earth formation, the magnetic fields in each of the sequences comprising at least an excitation pulse and at least one refocusing pulse, the plurality of sequences including at least one modified sequence having at least one modified pulse;

detecting spin echo signals induced by the at least one refocusing pulse in each of the sequences, the spin echo signals including spurious ringing signals from the excitation and at least one refocusing pulses, wherein the modified pulse causes a shift of a spin echo polarity for the spin echo signals associated with the modified pulse sequence relative to the polarity of spurious ringing signals from the excitation pulse associated with the modified pulse sequence; and combining corresponding spin echo signals from each of the plurality of sequences so as to provide combined spin echo signals in which spurious ringing induced by the excitation and the refocusing pulses has been substantially eliminated.

39. The method as defined by claim 38, further comprising inducing a static magnetic field in the earth formation prior to the inducing the plurality of sequences.

40. The method as defined by claim 38, wherein the inducing the sequences and combining the spin echo signals includes inverting phases of corresponding excitation and refocusing pulses in each of the sequences to obtain the substantial cancellation of the spurious ringing from the excitation and refocusing pulses.

41. The method as defined by claim 38, wherein the plurality of sequences comprises four sequences.

42. The method as defined by claim 41, wherein the combining comprises combining corresponding spin echo signals from two of the sequences and subtracting the spin echo signals from the other two of the sequences.

43. The method as defined by claim 41, wherein the spin echo signals of two of the four sequences have a polarity that is opposite to a polarity of the spin echo signals of the remaining two sequences.

44. A method for measuring nuclear magnetic resonance properties of an earth formation surrounding a wellbore, comprising:

inducing a first phase alternate pair of sequences of pulsed, radio frequency magnetic fields in the earth formation, the magnetic fields in each sequence of the first phase alternate pair comprising an excitation pulse and at least one refocusing pulse;

detecting spin echo signals induced by the at least one refocusing pulse in each of the sequences of the first phase alternate pair;

inducing a second phase alternate pair of sequences of pulsed, radio frequency magnetic fields in the earth formation, the magnetic fields in each sequence of the second phase alternate pair comprising an excitation pulse and at least one refocusing pulse, the excitation pulse in each sequence of the second pair having a polarity opposite to a polarity of the excitation pulse in each sequence of the first pair;

inverting a polarity of nuclear magnetic spins in each sequence of the second pair;

detecting spin echo signals induced by the at least one refocusing pulse in each of the sequences of the first phase alternate pair and the second phase alternate pair; and combining corresponding spin echo signals from each of the plurality of sequences so as to provide combined spin echo signals in which spurious ringing induced by the excitation and the refocusing pulses has been substantially eliminated.

45. The method as defined by claim 44, further comprising inducing a static magnetic field in the earth formation prior to the inducing.

46. The method of claim 1, wherein the modified pulse is an inverting pulse.

47. The method of claim 1, wherein the modified pulse comprises at least one refocusing pulse having a different phase than a series of refocusing pulses within the same pulse sequence.

48. The method of claim 1, wherein the modified pulse comprises changing the phase of at least one refocusing pulse within the pulse sequence.

49. The apparatus of claim 31, wherein the modified pulse is an inverting pulse.

50. The apparatus of claim 31, wherein the modified pulse comprises at least one refocusing pulse having a different phase than a series of refocusing pulses within the same pulse sequences.

51. The apparatus of claim 31, wherein the modified pulse comprises changing the phase of at least one refocusing pulse within the pulse sequence.

52. The method of claim 38, wherein the modified pulse is an inverting pulse.

53. The method of claim 38, wherein the modified pulse comprises at least one refocusing pulse having a different phase than a series of refocusing pulses within the same sequence.

54. The method of claim 38, wherein the modified pulse comprises changing the phase of at least one refocusing pulse within the sequence.

* * * * *